United States Patent [19]

Eberhard et al.

[11] Patent Number: 4,481,804

[45] Date of Patent: Nov. 13, 1984

[54] METHOD AND APPARATUS FOR CALIBRATION OF SENSORS

[75] Inventors: Patrick Eberhard, Allschwil; Wolfgang Mindt, Münchenstein; Jean-Pierre Palma, Pratteln; Robert Schäfer, Basel; Robert Schärf, Ramlinsburg, all of Switzerland

[73] Assignee: Hoffmann-La Roche Inc., Nutley, N.J.

[21] Appl. No.: 413,045

[22] Filed: Aug. 30, 1982

[30] Foreign Application Priority Data

Sep. 4, 1981 [CH] Switzerland .......................... 5721/81

[51] Int. Cl.³ ...................... G01L 27/00; G01N 27/26
[52] U.S. Cl. ......................................... 73/1 G; 204/406
[58] Field of Search ................. 73/1 G, 1 R; 204/1 T, 204/1 P, 400, 406, 415; 128/635, 204.22; 364/571; 324/74, 425

[56] References Cited

U.S. PATENT DOCUMENTS

| | | |
|---|---|---|
| 3,518,982 | 7/1970 | Timmins et al. |
| 3,981,297 | 9/1976 | Dunn et al. |
| 4,039,933 | 8/1977 | Moran ................................... 324/425 |
| 4,218,746 | 8/1980 | Koshiishi .............................. 364/571 |
| 4,269,684 | 5/1981 | Zick ........................................ 73/1 G |
| 4,321,113 | 3/1982 | Grambow et al. ..................... 73/1 G |
| 4,446,715 | 5/1984 | Bailey ..................................... 73/1 R |

FOREIGN PATENT DOCUMENTS 2030706 10/1980 United Kingdom .

Primary Examiner—Stephen A. Kreitman
Assistant Examiner—John E. Chapman, Jr.
Attorney, Agent, or Firm—Jon S. Saxe; Bernard S. Leon; Alan R. Stempel

[57] ABSTRACT

Calibration of sensors of the type used for the cutaneous determination of blood oxygen and carbon dioxide levels is facilitated by providing separate sensor units, alternatively and removably connectable to a calibration device and to the measuring devices with which they are used for such determinations. The sensor units contain, in addition to a sensor electrode, a data memory in which is stored calibration data generated when the sensor unit is connected to the calibration device. The calibration device can provide a plurality of calibration stations, each capable of supplying a standard gas to a connected sensor and, in response to signals from the sensor exposed to the standard gas, generating data signals representing the calibration of the sensor, which signals are transmitted to the data memory of the sensor unit. Upon connection of the sensor unit to the measuring device, the calibration data from the data memory of the sensor unit are used as a calibration base for measurements by the sensor.

9 Claims, 2 Drawing Figures

METHOD AND APPARATUS FOR CALIBRATION OF SENSORS

BACKGROUND OF THE INVENTION

1. Field of the Invention

This invention relates to a method of calibrating a sensor for determining the partial pressure of a gas, more particularly a cutaneous sensor for the cutaneous determination of blood oxygen and carbon dioxide levels, and to the apparatus for the implementation of the method. The term "calibration" as used herein is to be understood in the broad sense of covering both calibration and functional testing, i.e., testing the measurement characteristic of the sensor.

2. Description of the Art

It is fairly simple to calibrate oxygen sensors operating on the principle of the Clark electrode, since calibration can be performed using atmospheric air with the sensor electrode connected to the measuring device. Since during calibration the measuring device cannot be used for patient monitoring, a disadvantage of this method is that valuable operating time is lost. There is always a risk that the measuring device will need to be calibrated at the precise moment when it is urgently required. The only way of obviating this problem is for a hospital ward to have a correspondingly large number of devices available.

The problem is even more difficult in the case of carbon dioxide sensors. They cannot be calibrated using atmospheric air but must be calibrated by a special device which produces mixed gases suitable for calibration.

Theoretically it is unnecessary to provide a calibration device for each measuring device since a single calibration device can be used to calibrate a number of measuring devices. However, the problems just described in relation to oxygen sensors are further aggravated by the overlapping of the operating times of the measuring devices and the calibration device, so that in practice more calibration devices are needed than would be strictly necessary to calibrate a particular number of measuring devices. Also, to carry out a calibration the calibration device must always be brought to the measuring device or vice versa, thus imposing extra work on the personnel of a hospital.

The present invention provides a method of calibrating partial pressure sensors which obviates these disadvantages so that the measuring devices can be available for use permanently and at any required time.

SUMMARY OF THE INVENTION

In accordance with the invention, the sensor is operated and calibrated in a calibration device while it is separated from the measuring device and calibration data generated by the calibration device in accordance with the operation of the sensor are stored in a data memory connected to the sensor and, when the sensor is connected to the measuring device and put into use, the data are transferred to the measuring device and evaluated.

Advantageously, a number of sensors are calibrated in a single calibration device simultaneously or in sequence. Moreover, a functional check can advantageously be made simultaneously with the calibration.

Apparatus for the implementation of the method in accordance with the invention comprises a sensor unit, comprising a sensor and a data memory connected to the sensor, and a calibration device comprising means for mixing a standard gas, at least one calibration station at which the sensor is exposed to the standard gas, a program control means to which the sensor unit is connected during the calibration and a data processing and transfer means for storing in the data memory the calibration data derived from the operation of the sensor in the calibration device, together with any other relevant data desired to be stored. Advantageously, a number of measuring stations are provided.

According to a particularly advantageous feature of the apparatus, the sensor data memory is contained in the same housing as the contact device by means of which the sensor unit is connected to the calibration device or the measuring device. The form of coupling used by the contact device can be, for instance, galvanic or optical or inductive.

BRIEF DESCRIPTION OF THE DRAWINGS

An embodiment of the invention will be described hereinafter with reference to the accompanying drawing wherein.

DETAILED DESCRIPTION OF THE PREFERRED EMBODIMENT

Figure 1:
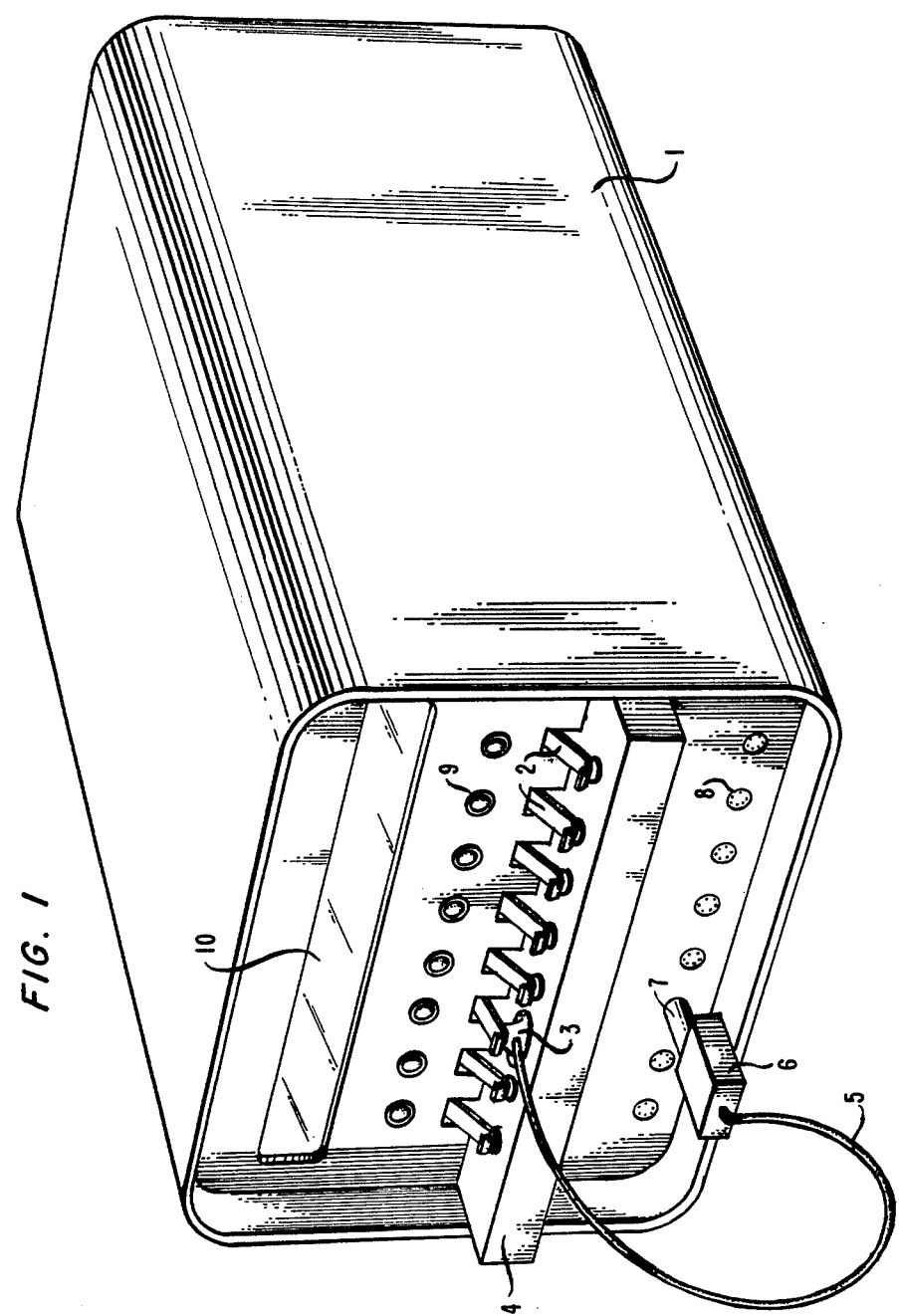
FIG. 1 is a perspective view of the exterior of a calibration device in accordance with the present invention.

The calibration device 1 shown in FIG. 1 has at the front a number of measuring stations 2 which receive the sensor electrodes of the sensor units. These measuring stations 2 are similar to the measuring stations or calibration chambers of conventional calibration devices such as the Calibration Unit 340 sold by the Kontron ® Company. Unlike conventional devices, however, the calibration device in this embodiment has eight measuring stations enabling eight sensors to be calibrated simultaneously or in a cyclic sequence. For constructional details of the measuring positions or stations reference is made to published descriptions of conventional calibration facilities.

Referring to FIG. 1, a cutaneous electrode 3 has been placed for calibration at the third measuring station. The electrode can be, for instance, a conventional cutaneous carbon dioxide partial pressure (pCO$_2$) electrode or one of the known combined electrodes for measuring both oxygen (pO$_2$) and carbon dioxide (pCO$_2$) partial pressures.

The electrodes need not be described herein in greater detail since the requisite information concerning them will be found in the relevant literature.

The cable 5 which in conventional apparatus would connect the sensor electrode 3 to the measuring device (not shown) extends instead to a connection unit 6 which is provided with a multi-pin plug 7. A jack 8 is associated with each measuring station 2. In the arrangement shown in FIG. 1 the unit 6 has its plug 7 plugged into the jack associated with the measuring station where the sensor electrode 3 is disposed.

The eight measuring stations are arranged on a console 4 in which the standard gases are conveyed to the measuring stations or calibration chambers. Arranged above each measuring station is an indicator lamp 9 indicating that the calibration and functional checks have been concluded and the electrode is ready for blood gas measurement.

An alphanumeric display 10 is arranged above the row of lamps 9 and serves in the present embodiment to display the nature of the malfunctioning of faulty sensors. Sensor specification data unconnected to malfunctioning can also be displayed. Information related to the calibration can also be shown, such as information about the standard gas being applied to the sensor when a number of different standard gases are involved.

Figure 2:
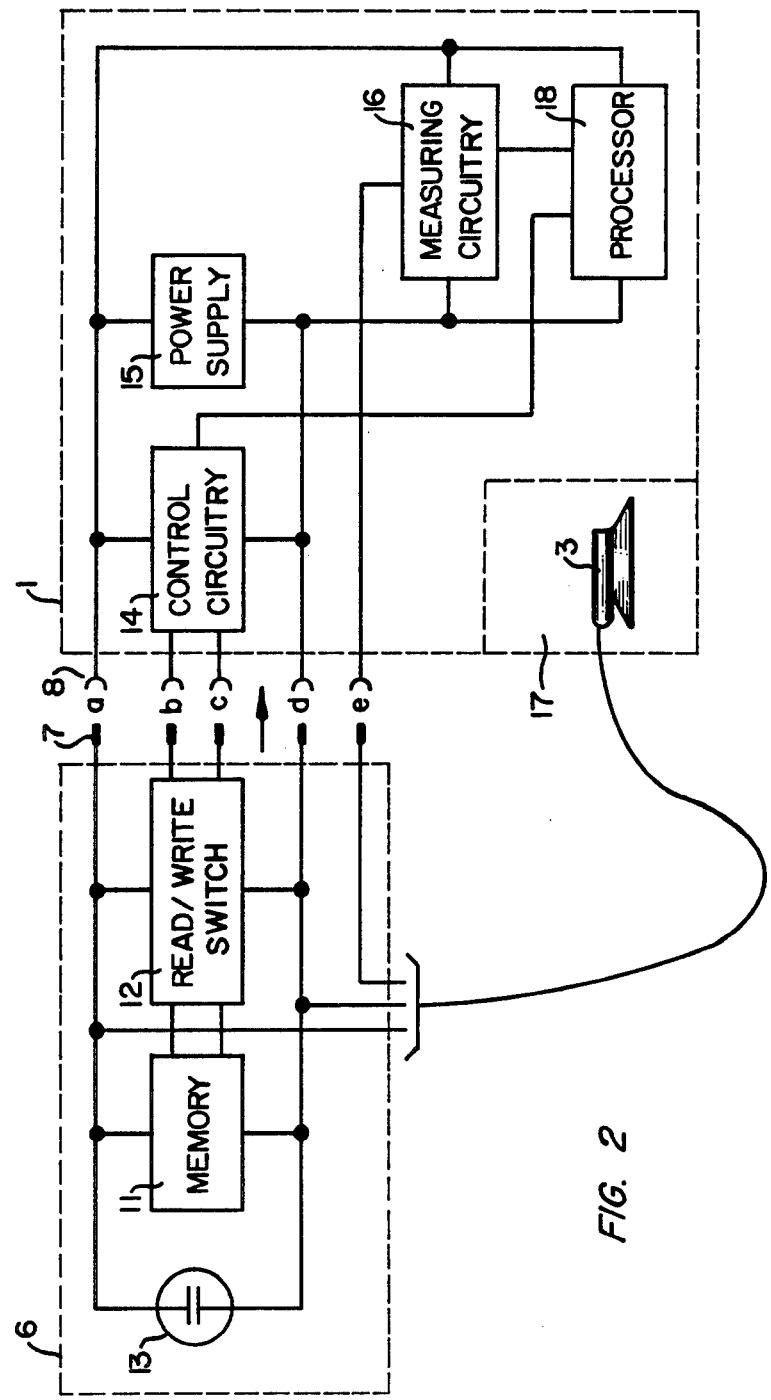
FIG. 2 is a block schematic diagram showing the basic circuitry of the calibration device and the sensor unit connected thereto.

The basic circuitry of unit 6 and those parts of device 1 cooperating with the unit 6 are shown in greater detail in block diagram form in FIG. 2. The unit 6 contains a memory 11 and a switch 12 controlling the writing into and the reading from the memory.

In one embodiment the memory 11 is a C-MOS shift register for which types 4031 (64 bit), 4517 (128 bit), or 4537 (256 bit) can, for instance, be used.

Other forms of memory can readily be used instead of a shift register, such as an electrically alterable read-only-memory (EAROM), a magnetic card or the like. A combination of various memories, e.g., a shift register with an EAROM, can be used to provide the desired functions.

In the above embodiment in which the memory element is a shift register, the switch 12 serves to disconnect the series input and output of data. In such an embodiment the switch 12 can be a type 4016 C-MOS analog switch.

In addition to these two logic elements, the unit 6 can contain a charge store 13 which in the embodiment shown takes the form of a capacitor having a sufficiently high capacitance, e.g. 0.1 farad. The charge store 13 serves to supply power for the shift register 11 for the period of time during which the unit 6 is isolated from the calibration device, in order to retain the stored data.

While the unit 6 is connected to the device 1, power is supplied by way of pins a and d of plug 7, the capacitor 13 also being charged by way of these pins. Pins b and c of plug 7 are for the input and output of data. Pin e provides a continuous connection to the measuring functions in the sensor electrode 3.

As already stated, unit 6 is connected to device 1 by way of the corresponding contacts of jack 8. Lines extend from contacts b, c to a bidirectional input-output circuit hereinafter designated the control circuit. The control circuit serves for writing into the shift register, the input signal and the timing signal being applied in the proper temporal sequence. The output of data from the memory 11 to the control device 14 follows a similar procedure. For the control circuit in the described embodiment, a type 8748 microprocessor is used.

The power is supplied to the device and to the unit 6 by a power supply circuit 15.

Block 16 represents the remaining circuitry of the measuring device, such circuitry basically corresponding to the circuitry of a conventional $pO_2$ or $pCO_2$ measuring device without the data storage facility in accordance with the invention. Since the constructions involved in this part of the arrangement are conventional and known, no further details need be given here, reference being made to appropriate publications showing such arrangements.

A processor unit 18 provides the program required for calibration and also provides a functions check by evaluation of the data that comes from the measuring circuitry 16 of the device. For the processor unit 18 in the described embodiment, a type 8085 microprocessor is used.

Referring to FIG. 2, the measurement stations or calibration chambers are indicated as a part of the calibration device in the form of a block 17 bounded by broken lines. When the electrode 3 is at a measuring station in the manner shown in FIGS. 1 and 2 and the plug 7 has been connected to the jack 8, the program for calibrating the electrode 3 can proceed as the processor 18 and the remaining circuitry 16 go into operation. The calibration data are then supplied by way of control circuit 14 and analog switch 12 to memory 11. When the sensor is then removed from the calibration device and connected to a measuring device, the calibration data are transferred to the latter and processed during measurement conventionally just like conventionally measured calibration data.

The charge store 13 enables the calibration data to be stored for a time when the sensor has been separated from the calibration device. Since the charge of the store 13 is eventually consumed, the memory 11 loses its information after a certain time. This is not undesirable because a calibration should not be older than, for instance, 24 hours. A calibration becomes invalid after a longer time. The measuring device has means for giving a malfunction alarm when a sensor whose memory is devoid of calibration data is used. A warning system of this kind can readily be devised by those skilled in the art, using the ordinary knowledge to be expected of such a person.

The calibration data, i.e., either the measurement data obtained with the sensor concerned and the standard gases used or a correction value calculated from such measurement data, are written into the memory 11. The memory can also be provided with other data characteristic of the sensor. If the data memory in the unit 6 is required to contain data which, unlike the calibration data, are for long term storage, it is necessary to provide in addition to the shift register a memory which preserves the data independently of the power supplied by a charge store. Alternatively, a battery can be provided instead of the charge store.

Typical data transferred to the memory include the time of calibration, sensor identification, the measurement characteristic of the sensor at the time of calibration and other items.

The galvanic coupling represented by the plug 7 and jack 8 can be replaced by some other form of coupling, such as optical or inductive coupling, thus enabling requirements for the patient isolation to be met at this point. The construction of an optical or inductive coupling of this kind is known and can readily be carried out by those skilled in the art.

What is claimed is:

1. A method for determining the partial pressure of a sample gas by means of a sensor wherein said sensor is initially exposed to a standard reference gas for calibration and thereafter to said sample gas for measurement, said method comprising the steps of:
   (a) providing as apparatus for the conduct of said determination
       (1) an independent and separate sensor unit which includes a partial pressure sensor and a data memory device.
       (2) an independent and separate calibration device, and
       (3) an independent and separate measuring device for receiving and processing measurement signals from said partial pressure sensor when said sensor is exposed to a sample gas;

said sensor unit being removably connectable alternatively to either said calibration device or to said measuring device, wherein said calibration device, when connected to said sensor unit, generates calibration data in response to exposure of said partial pressure sensor to said standard reference gas and transfers said calibration data to said data memory device of said sensor unit, and wherein said measuring device, when connected to said sensor unit, receives said calibration data from said data memory device and utilizes said calibration data in the processing of measurement signals from said partial pressure sensor;

(b) connecting said sensor unit to said calibration device and, while so connected, exposing said partial pressure sensor to said standard reference gas and storing in said data memory device of said sensor unit calibration data generated by said calibration device; and (c) thereafter disconnecting said sensor unit from said calibration device, connecting it to said measuring device, allowing the transfer of calibration data from said data memory device to said measuring device and, while said sensor unit is so connected, exposing said partial pressure sensor to said sample gas so that said sensor provides measurement data to said measuring device.

2. The method of claim 1 wherein said partial pressure sensor is a cutaneous sensor for cutaneous determination of levels of one or more of oxygen and carbon dioxide in the blood.

3. A system for determining the partial pressure of a sample gas, said system comprising:

(1) an independent and separate sensor unit which includes a partial pressure sensor and a data memory device, (2) an independent and separate calibration device; and (3) an independent and separate measuring device for receiving and processing measurement signals from said partial pressure sensor when said sensor is exposed to a sample gas;

said sensor unit being removably connectable alternatively to either said calibration device or to said measuring device, wherein, said calibration device, when connected to said sensor unit, generates calibration data in response to exposure of said partial pressure sensor to said standard reference gas and transfers said calibration data to said data memory device thereof, and wherein said measuring device, when connected to said sensor unit, receives said calibration data from said data memory device and utilizes said calibration data in the processing of measurement signals from said partial pressure sensor.

4. A calibration device for use with a sensor unit including a partial pressure sensor and data memory means, wherein a sensor unit is removably connectable either to said calibration device or to a separate measurement device, said calibration device comprising:

separable connector means for allowing a sensor unit to be operatively but removably connected to said calibration device, in order to permit the transfer of signals therebetween;

measuring circuit means for receiving the signal generated by the partial pressure sensor of a sensor unit connected to said calibration device and for generating an output in response thereto;

processing circuit means for evaluating the output generated by said measuring circuit and for generating calibration data in response thereto; and control circuit means for transferring said calibration data to the data memory means of said sensor unit.

5. A calibration device in accordance with claim 4 which further includes station means for exposing the partial pressure sensor of a sensor unit connected to said calibration device to a standard reference gas.

6. A sensor unit for use in conjunction with a measuring device for measuring the partial pressure of a gas, said unit comprising:

a partial pressure sensor; data memory means; and separable connector means for allowing the operative but removable connection of said sensor unit to either a separate calibrating device or to a separate measuring device, in order to permit the transfer of signals therebetween;

wherein, when said sensor unit is connected to said calibration device, said data memory means thereof is capable of receiving and storing calibration data pertaining to said partial pressure sensor which is generated by said calibration device upon exposure of said sensor to a standard reference gas; and further wherein, when said sensor unit is thereafter connected to said measuring device said data memory means is capable of transferring said calibration data stored therein to said measuring device, which utilizes said calibration data in processing measurement signals from said partial pressure sensor.

7. A sensor unit according to claim 6 wherein said data memory means is mounted within said separable connector means.

8. A sensor unit according to claim 6 wherein said connector means is a multiple contact element, separable electrical connector.

9. A sensor unit according to claim 6 wherein said partial pressure sensor is a cutaneous sensor for cutaneous determination of levels of one or both of oxygen and carbon dioxide in the blood.

* * * * *